United States Patent [19]

Siddiqi et al.

[11] Patent Number: 4,607,010
[45] Date of Patent: Aug. 19, 1986

[54] ANALYTICAL PROCESS AND MEANS FOR MEASURING PROTEASE INHIBITOR CAPACITY OF SERUM

[75] Inventors: Iqbal Siddiqi, Geneva, Switzerland; Jean Brochot, Bellegarde, France; Ranald M. Sutherland, Carouge, Switzerland

[73] Assignee: Battelle Memorial Institute, Geneva, Switzerland

[21] Appl. No.: 620,260

[22] Filed: Jun. 13, 1984

[51] Int. Cl.$^4$ ............... C12Q 1/38; C12N 9/99
[52] U.S. Cl. ................... 435/23; 435/184; 204/403; 204/419; 204/1 T
[58] Field of Search ............ 435/4, 7, 23, 24, 184, 435/188; 204/1 F, 403, 419

[56] References Cited

U.S. PATENT DOCUMENTS

| | | | |
|---|---|---|---|
| 4,303,592 | 12/1981 | Laura et al. | 260/543 F |
| 4,353,983 | 10/1982 | Siddiqi | 435/28 |
| 4,430,263 | 2/1984 | March et al. | 260/112 R |

OTHER PUBLICATIONS

Bergmeyer, *Methods of Enzymatic Analysis*, vol. 1, Academic Press, Inc., New York, 121-123, 131-134 (1974).
Eckfeldt et al, Chemical Abstracts, 97:2597b, 266 (1982).
Erlanger et al, Chemical Abstracts, 72:86503n, 35 (1970).
J. H. Eckfeldt et al, Clin. Chem., 1982, vol. 28, pp. 1108–1112.
J. Wenger and M. Sundy, Clin. Chem., 1974, vol. 20, pp. 328–331.
F. Miesch et al, Clin. Chem. Acta., 1971, vol. 31, p. 365.
S. Erikson, Acta. Med. Scand., 1965, vol. 177, suppl: 432.
N. Berg and Erikson; N.E.J. Med., 1972, vol. 287, pp. 1264–1267.
J. O. Jeppsson, C. B. Laurell and B. Franzen, Clin. Chem., 1979, vol. 25; pp. 629–638.
T. Chase and E. Shaw; Biochem. Biophys. Res. Commun., 1967, vol. 29, pp. 508–514.
B. E. Erlanger and R. A. Sack; Anal. Biochem., 1970, vol. 33, pp. 318–322.
J. A. Pierce; New England J. Med., 1972, vol. 287, p. 1905.
L. Gaidulis et al, Clin. Chem., 1983, vol. 29, pp. 1838–1840.
"Alpha$_1$-Antitrypsin", by A. Myron Johnson, Beckman Instruments, Inc., ICS 12r.

*Primary Examiner*—Esther M. Kepplinger
*Attorney, Agent, or Firm*—Cushman, Darby & Cushman

[57] ABSTRACT

An analyte sample of blood serum is reacted with a protease in excess over that quantity required to provide a 1:1 protease:inhibitor complex. The excedent protease is then back-titrated using the reaction with diphenylcarbamyl fluoride and measuring electrometrically the liberated fluoride.

7 Claims, 8 Drawing Figures

ANALYTICAL PROCESS AND MEANS FOR MEASURING PROTEASE INHIBITOR CAPACITY OF SERUM

FIELD OF INVENTION

The present invention embodies an electrometric detection method for use in quantitative determination of protease inhibitor capacity of serum. Following the reaction of protease inhibitors with an excess but known amount of an active protease enzyme, the remaining fraction of the active enzyme is then measured by titrating the active-sites of the enzyme with diphenylcarbamylfluoride and concommittant release of fluoride ions $F^-$. The release of $F^-$ is measured electrometrically by a fluoride ion-selective electrode. Inherent in this invention is the facility to monitor the electrode signal in a continuous fashion thus allowing kinetic or reaction-rate monitoring which offers, in turn, the opportunity for a simple and rapid analytical system.

BACKGROUND OF THE INVENTION $\alpha_1$-Antitrypsin ($\alpha_1$-AT), $\alpha_2$-Macroglobulin ($\alpha_2$M) and $\alpha_1$-antichymotrypsin account for about 90% by weight of the total plasma protease inhibitors. The three inhibitors are high molecular weight glycoproteins and are capable of inhibiting various proteolytic enzymes containing active-site serine residues. They act by allowing their target proteases to bind directly and irreversibly to a substrate-like region within the amino acid sequence of the inhibitor. In almost all cases, the resulting complex is of 1:1 stoichiometry i.e. one molecule of each reactant. This property forms the basis of a variety of serum protease inhibitor capacity assays utilizing trypsin or chymotrypsin as proteases (J. H. Eckfeldt et. al., Clin. Chem. 1982, vol. 28, pp 1108–1112 and J. Wenger and M. Sundy, Clin. Chem. 1974, vol. 20, pp 328–331). In most tryspin or chymotrypsin inhibitor capacity assays it has been shown that $\alpha_1$-AT is invariably measured (F. Miesch et al. Clin. Chem. Acta. 1971 vol. 31 pp 231 and above mentioned references).

$\alpha_1$-Antitrypsin, due to its functional relationship in various disease states, is subject of importance at clinical diagnostic level. Deficiency of $\alpha_1$-AT can arise due to specific genetic defects in certain individuals. This leads to a lung disease, familial emphysema, at an early age (S. Erikson, Acta. Med. Scand., 1965, vol. 177, suppl: 432), liver disease (N. Berg and Erikson; N.E.J. Med., 1972, vol. 287, pp 1264–1267). About 5 to 20% of infants with inherited $\alpha_1$-AT deficiency suffer from infantile liver cirrhosis leading to fatal hepatic failure or hemorrhage during childhood (H. L. Sharp; Gastro, 1970, vol. 70, pp 611621).

The most common (nongenetic) change is due to the acute phase response where $\alpha_1$-AT levels are elevated in most conditions associated with infection, inflammation or tissue necrosis (J. O. Jeppsson, C. B. Laurell and B. Franzen, Clin. Chem 1979, vol. 25; pp 629–638). Elevation is rapid, within 24 hours of the stimulus, and continues for as long as the stimulus is present. Increased $\alpha_1$-AT synthesis is also seen with pregnancy, oestrogen therapy and some forms of hepatocellular disease. $\alpha_1$-AT levels are reduced in association with neonatal respiratory distress syndrome.

Overall, the major clinical interest is $\alpha_1$-AT deficiency, especially where neonatal screening can detect the genetically based hepatic diseases before becoming clinically apparent. There is also a role in the detection of heterozygotes where genetic counselling is indicated. $\alpha_1$-AT measurement is useful for monitoring acute phase responses and there may be a role for $\alpha_1$-AT measurement in the prediction and monitoring of neonatal idiopathic respiratory distress syndromes.

Despite its importance, the measurement of protease inhibitor capacity has not found widespread use because most assays are manual, laborious and, in a number of cases, employ complex and expensive instrumentation. In addition, the lack of absolute standardization in the current assays is a serious problem and prevents meaningful interlaboratory comparison. Most of these assays are based on the inhibition of trypsin or chymotrypsin and the results are expressed as inhibition either as per mass of enzyme or as per units of enzyme activity inhibited by a given volume of serum. The use of mass is, however, incorrect because commercially available crystalline enzymes are not 100% enzymatically active and $\alpha_1$-AT reacts with only active enzyme fraction. The operational molarity of these enzymes could easily vary between 40 to 70% of the mass as shown by active-site titration techniques (T. Chase and E. Shaw; Biochem. Biophys. Res. Commun., 1967, vol. 29, pp 508–514 and B. E. Erlanger and R. A. Sack; Anal. Biochem., 1970, vol. 33, pp 318–322). The use of the enzyme units inhibited per volume of serum also has drawbacks. The substrates most commonly used have limited solubility and enzymes are operating at nonsaturating substrate concentration. This condition, commonly referred to as non zero-order kinetics, makes the estimation of enzyme activity very sensitive to small variations in substrate concentration.

Immunochemical techniques offer the advantage of high specificity but these techniques do not distinguish enzymically active complexes from inactive complexes (J. A. Pierce; New England J. Med. 1972, vol. 287, pp 1905 and L. Gaidulis et. al., Clin. Chem., 1983, vol. 29, pp 1838–1840).

Most of the current assays are furthermore based on photometric techniques, which, beside requiring expensive intrumentation, work satisfactorily only with test solutions of certain optical purity. Thus highly turbid, lipemic or icteric serum can be problemetic in these assays.

The main aim of the present invention is to provide an improved method for the assay of protease inhibitor capacity of serum. A further aim of the present invention is to provide a method which can unambiguously measure serum protease inhibitor capacity by using an active-site titration technique independent of test protease enzyme supplier, and which does not require optically pure test solution. A still further aim of the present invention is to provide means to perform these assays with inexpensive instrumentation and which may be readily automated.

Assays for serum protease inhibitor capacity are generally based on the stoichiometric 1:1 combination of the inhibitor with an excess and known amount of trypsin or chymotrypsin. Since the resulting complex is enzymically inactive, the remaining active fraction of the enzyme provides a measure of serum inhibitor capacity. It has now been found that the serum inhibitor capacity assay is improved and greatly simplified by employing a specific active-site titrant for the direct determination of the enzyme. Active-site titrants are an art recognized class of enzyme reagents and are frequently employed in the determination of the "operational concentration" of enzymes. An active-site titrant is a nonprotein substance and a specific inactivator of a given enzyme. The titrant reacts mole for mole with some amino acid residues in the active-site of the enzyme. The reaction principle may be represented by the following equation.

where RL is the active-site titrant, R-Enzyme is the titrated inactive enzyme complex and L* is the product released which, depending on its nature, can be measured by a number of available sensitive techniques. In the case of serum protease inhibitor capacity assays this principle has recently been exploited using photometric detection technique (J. H. Eckfeldt et. al., Clin. Chem. 1982, vol. 28, pp. 1108–1112). Although this publication clearly shows the advantage of active-site titration, the requirement of expensive instrumentation is its serious drawback. The present invention utilizes the known phenomenon that diphenylcarbamyl fluoride (DPCF) is a specific inactivator of $\alpha_1$-chymotrypsin and trypsin and can be used as active-site titrant. The DPCF reaction is stoichiometric with the release of $F^-$ ion which then can be measured by a fluoride ion-selective electrode (B. F. Erlanger and R. A. Sack, Anal. Biochem., 1970, vol. 33. pp 318–322).

We have found that the technique used for active-site titration as described in the above mentioned publication can not be used for the assay of serum protease inhibitor capacity for the following reasons:

(i) The active-site titration requires at least 30 minutes of incubation prior to $F^-$ measurement which is somewhat inconvenient if a large number of serum samples are to be processed as in screening studies.

(ii) The lack of constant ionic strength buffer can be a serious source of error in $F^-$ measurement by the fluoride ion-selective electrode.

(iii) In actual serum protease inhibitor capacity assays, the 30 minute incubation with DPCF for active-site titration of chymotrypsin results in anamalous $F^-$ ion generation probably due to some unexplained reactions with the test serum components.

DESCRIPTION OF THE INVENTION

We have now discovered that the above mentioned problems can be completely eliminated or reduced to insignificant levels by applying the analytical method which comprises reacting an analyte sample of blood serum with a known excess of a 1:1 complex forming protease enzyme partner to the inhibitor of interest and thereafter back-titrating the excedent of the protease over that required to form the 1:1 complex by the reaction with diphenylcarbamyl fluoride and electrometrically determining the ionic fluoride quantitatively generated in this reaction, the electrometric determination involving measuring the rate of generation of the fluoride and matching the slope of the rate curve thus obtained against standard slopes obtained identically from standard amounts of the protease, and preferably, using total ionic-strength adjusting buffer in the range of pH from 5.5 to 7.25 and by measuring the rate of active-site titration. The ionic strength and the pH of the buffer can be varied widely as long as there is no significant alteration in the ionic strength on addition of serum sample and the pH is maintained in the region where rate of reaction of chymotrypsin with serum protease inhibitors or DPCF is not significantly altered. In the present invention, the ionic strength of 0.2 to 0.5 and pH of 5.5 to 7.25 are preferred but are not limiting since a range of ionic strength 0.1 to 1 and a range of pH 5 to 8 are possible with proper adaptation of the system to each individual value in said range. Since the rate of $F^-$ generation is proportional to the amount of active chymotrypsin, the serum inhibitor capacity can be measured by the loss in activity of known chymotrypsin solution.

The $F^-$ concentration is measured as a function of time, electrometrically with an electrode which is both very sensitive and selective and selective to $F^-$, such as the electrode type "96-09" made by Orion Research Inc., Cambride, Mass. U.S.A.

In order to demonstrate the subject invention, the following assays were carried out. These assays are offered by way of illustration and are not to be constituted as limiting. The annexed drawing helps in comprehending the assay results.

EXAMPLE 1

Figure 1:
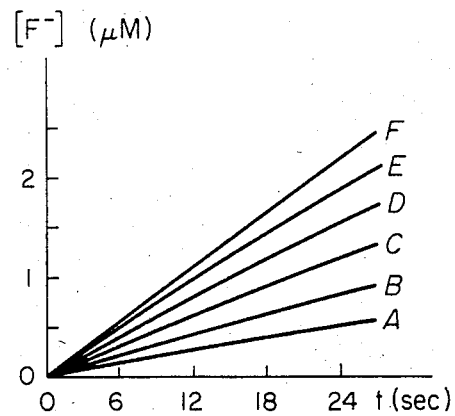
FIG. 1 is a graph showing the rate of $F^-$ formation as a function of time in the electrometric titration of six different standard concentrations of chymotrypsin by an excess of DPCF.

REACTION-RATE ASSAY OF ACTIVE α-CHYMOTRYPSIN (a) Preparation of Diphenylcarbamyl Fluoride (DPCF)

DPFC was prepared according to a published method of Metzger and Wilson (Biochem., 1964, Vol. 3, pp 926–931). Diphenylcarbamyl Chloride was obtained from Aldrich Chemical Co. Inc., Milwaukee, Wis., USA. DFPC was prepared from the chloride by reaction with 50% excess antimony trifluoride in hot xylene for one hour. The mixture was cooled to room temperature. Antimony halides were then precipitated with ether and the solution decolorized with charcoal, filtered and evaporated to dryness. The solids thus obtained were dissolved in Methanol, decolorized with charcoal, filtered and crystalyzed by cooling the solution to about 0° C. This process was repeated again and yielded white crystals with melting point of 81°–82° C.

(b) Reagent Solutions

The following reagent solutions were prepared:
(1) Assay buffer 1-pH 5.5 and ionic strength of 0.36 was prepared by dissolving glacial acetic acid 14.41 g (0.240M), sodium hydroxide 8.525 g (0.213M), sodium chloride 5.077 g (0.087M) and calcium chloride 2.220 g (0.020M) in about 600 ml of double-distilled water. Sodium fluoride solution (1.0 mM) 10 ml was then added and made up to 1 L with doubly distilled water.
(2) Chymotrypsin Stock Solution: Crystalline $\alpha$-chymotrypsin, 62.5 mg was dissolved in 5 ml of 2 mM HCl solution. On a strictly weight basis the stock solution is 500 $\mu$M. Chymotrypsin working solutions of 100, 200, 300 and 400 $\mu$M were prepared by appropriate dilution of stock solution in 2 mM HCl. The solutions were kept in ice prior to their use. In the making of standards samples of chymotrypsin corresponding to the following quantities were used: A 2 $\mu$M, B 4 $\mu$M, C 6 $\mu$M, D 8 $\mu$M, E 10 $\mu$M and F 12 $\mu$M.
(3) DPFC solution 5 mM in 50% methanol was prepared by dissolving 21.5 mg of DPFC in 10 ml of methanol and then making up to 20 ml with double distilled water.

(c) Assay Procedure applied to the making of standards

Into a small (10 ml capacity) polypropylene beaker, 4.8 ml of assay buffer and 100 $\mu$l of a chymotrypsin working solution containing the required quantity corresponding to standards A to F were pipetted. The solution during the entire assay was stirred by a miniature teflon-coated magnetic bar. Active-site titration of the chymotrypsin involving $F^-$ generation was then carried out in the following manner: fluoride ion-selective electrode (type 96-09 Orion Research Inc. Mass., USA) was then inserted in the solution. This electrode had a reference electrode combined therewith but any other fluoride electrode with separate reference electrode can also be used. The electrode can be connected to any suitable voltmeter and in the present invention, a Corning EEL 112 Digital Research pH Meter (Corning Scientific Inc., Mass., USA) was used. Following immersion, the electrode potential was allowed to stabilize for a strictly fixed time and in the present invention 3 minutes were adequate. Immediately after electrode stabilization, 100 $\mu$l of DPFC solution was injected and the electrode potential in mV (relative) was measured every successive 3 seconds for 30 seconds. The concentration of $F^-$ for each measurement interval was calculated from the measured potential by the Nernst equation which in this case has the form:

$$E = E' - S \log [F^-]$$

where $E'$ is a constant inherent to the system which is determined experimentally and which involves activity factors and the liquid junction potentials. S is the "Nernst slope" which is also a constant and is approximately 59 mV for a change of 10 units in the concentration of $F^-$ where the latter is expressed in moles/l. Reaction-rate curves thus obtained are shown in FIG. 1 each curve A to F representing the rate measured with corresponding samples A to F. The rate of $F^-$ generation was calculated by linear regression of the $dF^-/dt$ in the ascending portion of each curve.

In order to assess the precision of the technique, each chymotrypsin solution was measured in triplicates. A blank was also measured by injecting 100 $\mu$l of 2 mM HCl solution in place of chymptrypsin solution. The slope values for each rate determination A to F obtained are plotted against chymotrypsin amount and shown in FIG. 2 (standard) which clearly demonstrates the linear relationship between active chymotrypsin concentration and rate of active site titration reflected in the $F^-$ released.

Figure 2:
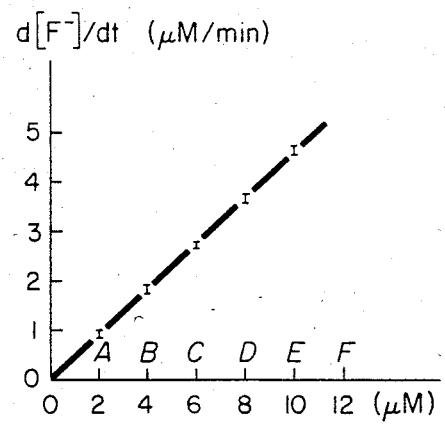
FIG. 2 is a graph of the slopes of the rate curve of FIG. 1 against the corresponding concentrations of chymotrypsin.

For actual analysis of unknown serum analytes, the analyte was first reacted with a known excess of chymotrypsin and the remainder of the reagent was ascertained according to the above technique, the slope of the rate curve being compared to the standard curve of FIG. 2 for obtaining the desired result of residual chymotrypsin. Then this result was subtracted from the initial amount used wherefrom the result on the inhibitor in the serum was obtained.

EXAMPLE 2

FIXED TIME ASSAY OF ACTIVE $\alpha_1$-CHYMOTRYPSIN AND TRYPSIN (comparative example)

Diphenylcarbamyl fluoride is a specific inactivator for both $\alpha$-chymotrypsin and trypsin. The kinetics of inactivation for trypsin at pH 5.5 is however, considerably slow and hence the reaction-rate assay at this pH was unsuitable. The fixed time pseudoequilibrium can nevertheless be used for the assay of both enzymes since the number of moles of $F^-$ released is stoichiometrically related to the active concentration of either two enzymes.

The reagent solutions were the same as described in Example 1. The assay procedure was however modified in the following manner. Into the plastic beaker, 4.8 ml of assay buffer, 100 ml of either enzyme solution and 100 $\mu$l of DPFC solution were added. A blank was prepared in a similar manner by substituting 100 $\mu$l of a 2 mM HCl for the enzyme solution. All solutions were left at room temperature for two hours. Following that the $F^-$ concentration was then measured by the fluoride electrode. The active concentration of the enzyme as percentage of the total mass of enzyme used was then calculated as follows:

$$\% \text{ Active Enzyme} = \frac{\text{Moles of F Measured}}{\text{Moles (Mass) of Enzyme Used}} \times 100.$$

The active concentration of both enzymes was measured between 2 to 10 $\mu$M (mass) and the results are shown in Table 1.

TABLE 1

| Enzyme concentration | $F^{-*}$ $\mu$M (mass) | % Active $\mu$M | Mean ± Stand. Dev. |
|---|---|---|---|
| (a) Trypsin: | | | |
| 2 | 12.12 | 77.5 | |
| 5 | 14.00 | 69.4 | 70.9 ± 4.9 |
| 10 | 17.12 | 65.7 | |
| (b) Chymotrypsin | | | |
| 2 | 12.20 | 80.0 | |
| 5 | 14.21 | 72.2 | 74.2 ± 4.2 |
| 10 | 17.64 | 70.4 | |
| (c) Blank | 10.60 | — | — |

*Mean of duplicates.

This comparative example clearly shows that the use of mass is meaningless and only a certain fraction of the total enzyme mass is active.

EXAMPLE 3

FIXED TIME ASSAY OF SERUM PROTEASE INHIBITOR CAPACITY (comparative Example)

Figure 3:
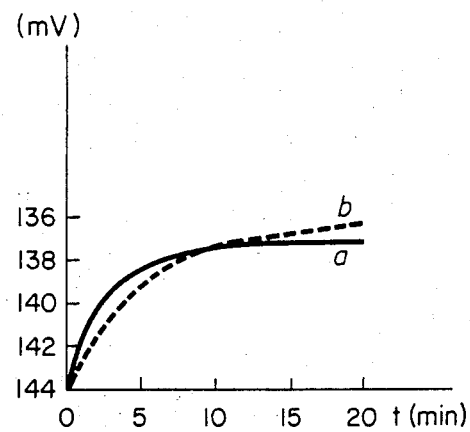
FIG. 3 is a graph showing the rate of $F^-$ liberation with time in the fixed time electrometric titration of chymotrypsin (a) and serum inhibited chymotrypsin (b). This is a comparative illustration.

The fixed time equilibrium method for the active-site titration as in example 2 and described by Erlanger and Sack (Ref. Cited) was investigated for its applicability in the assay of serum protease inhibitor capacity. The reagents and assay procedure were similar as described in example 2, but with the following modifications: assay buffer 4.7 ml, chymotrypsin solution 100 µl, DPFC solution 100 µl and serum sample 100 µl. The assay buffer, chymotrypsin and serum were incubated for 3 minutes in the beaker with the fluoride electrode immersed there in. When 3 minutes have elapsed, the DPCF solution was added the $F^-$ generation was allowed to proceed for 20 minutes. The time course of $F^-$ generation with chymotrypsin alone and chymotrypsin with serum is shown in FIG. 3. Surprisingly the $F^-$ generated in the presence of serum was higher than $F^-$ concentration with chymotrypsin alone. This may be due to certain slow reactions of DPFC with some serum components which become highly significant only when the assay requires long periods of reaction. Similar result was obtained when trypsin was substituted for chymotrypsin.

EXAMPLE 4

REACTION-RATE ASSAY OF SERUM PROTEASE INHIBITOR CAPACITY

In this example, serum protease inhibitor capacity assay by reaction-rate method of active-site titration is demonstrated. The absolute reaction-rates are unimportant and the relative rates from uninhibited and serum inhibited reactions are adequate.

The reagents used were the same as described in Example 1. The serum sample used was obtained from the local hospital. Into the plastic beaker 4.6 ml of assay buffer was pipetted and the fluoride electrode immersed therein. While stirring the solution, 100 µl of standard chymotrypsin solution estimated to be in excess of the required quantity to block the inhibitor under investigation and a known volume of serum (varying between 40–150 µl) were added. Depending upon the volume of serum, a corresponding volume of normal saline (0.15M NaCl) was then added so as to maintain the total test volume (serum=saline) constant at 200 µl. The solution was then left to equilibrate for exactly 3 minutes. This serves two functions: (i) allows the interaction of serum protease inhibitors with chymotrypsin; (ii) stabilization of electrode potential. The duration is however, not critical, provided it is maintained constant in all assays. Following 3 minutes, 100 µl DPCF solution was injected and the rate of $F^-$ generation was measured as described in Example 1. The relative rate of uninhibited chymotrypsin was determined by substituting 200 µl of saline for serum. The percent inhibition due to serum were then calculated from the difference in the relative rates of chymotrypsin alone and serum inhibited chymotrypsin. The results are summarised in Table 2.

TABLE 2

| Normal saline (NaCl 0.9%) | Serum | $dF^-/dt$* | % Inhibition |
|---|---|---|---|
| 200 | 0 | 5.02 ± 0.04 | 0 |
| 160 | 40 | 4.29 ± 0.08 | 14.54 |
| 140 | 60 | 4.02 ± 0.09 | 19.92 |
| 120 | 80 | 3.84 ± 0.01 | 23.50 |
| 100 | 100 | 3.65 ± 0.03 | 27.29 |
| 80 | 120 | 3.40 ± 0.07 | 32.27 |
| 50 | 150 | 3.13 ± 0.14 | 37.65 |

*Mean of triplicate measurements with Std. Dev.

Figure 4:
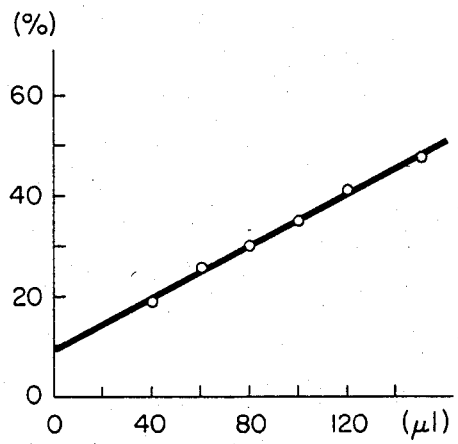
FIG. 4 is a graph showing the % inhibition (Y axis) of a standard chymotrypsin sample by increasing amounts of serum containing chymotrypsin inhibitors (X axis).

FIG. 4 clearly shows that the inhibition of chymotrypsin (% inhibition is plotted on the Y axis) was linear with respect to the volume of serum in the test.

EXAMPLE 5

REACTION-RATE ASSAY FOR α-CHYMOTRYPSIN AND TRYPSIN

The reaction-rate assay at pH 5.5 although adequate for chymotrypsin is not suitable for trypsin. At pH 7.25, the rate of $F^-$ liberation was found to be considerably higher for both chymotrypsin and trypsin. The DPCF solution, however, at this pH is rather unstable, perhaps due to slow hydrolysis. Fixed time assays involving long incubations therefore cannot be used. Rapid reaction-rate technique according to the invention can be used for the assay of both chymotrypsin and trypsin provided that DPCF-enzyme reaction is limited to 60 to 90 seconds and preferably within 60 seconds. The actual assays for the two enzymes were performed in the following manner:

1. Assay buffer 2. pH 7.25 and ionic strength 0.26. Sodium cacodylate (0.2M) was dissolved in about 800 ml of double distilled water. The solution pH was adjusted to 7.25 by addition of 1M HCl. Calcium chloride 2.22 g (0.02M) and 10 ml of 1 mM solution of sodium fluoride (10 µM) were then added and entire solution made up to 1 liter.
2. Chymotrypsin solutions were prepared as described in Example 1.
3. Trypsin solutions: 500 µM stock solution was first prepared by dissolving 62.5 mg of trypsin in 5 ml of 2 mM HCl. Appropriatedilution of this stock solution with 2 mM HCl were then made to provide working trypsin solutions of 50, 100, 150, 200 and 250 µM. They enabled to provide standard quantities of trypsin in the standard control tests, i.e. G 1 µM to K 5 µM.
4. DPCF solution was prepared as described in Example 1.

Figure 5:
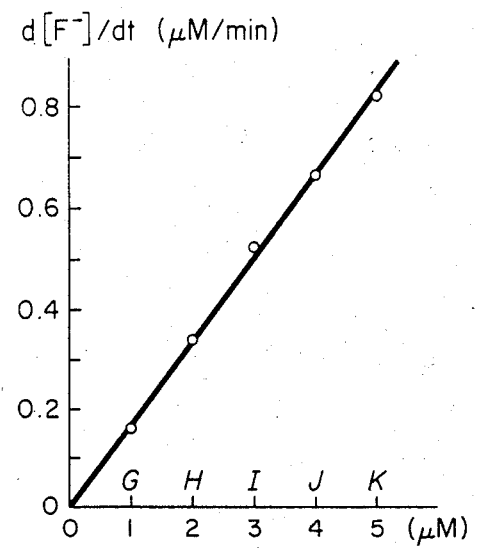
FIG. 5 is a graph in which the slopes of the rate curves corresponding to electrometrically determined trypsin standards have been plotted against the effective concentration values of the standards.

Assay procedure: The assay procedure for trypsin was the same as described in Example 1. The reaction-rate curves were comparable to the chymotrypsin curves at pH 5.5 described with reference to FIG. 1. The slopes of these curves were plotted, after correction for the blank, against the actual amount of trypsin tested. This is shown in FIG. 5 where the standards G to K follow the X axis and the slopes in µM of $F^-$ per min are on the Y axis. The rate of $F^-$ generated was found to be linear.

Figure 6:
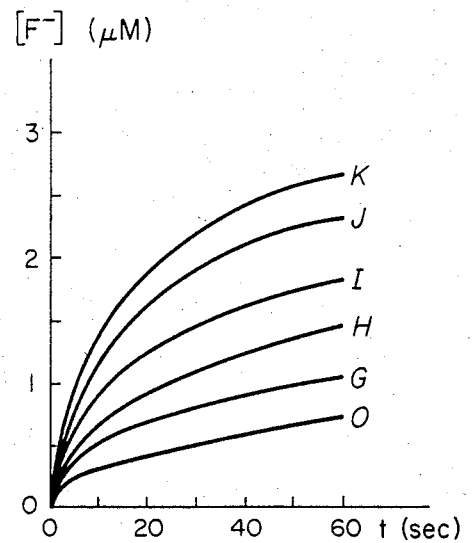
FIG. 6 is a graph showing the $F^-$ liberation rate curves for a series of standard chymotrypsin samples at pH 7.25; note that the rates are higher at pH 7.25 than at pH 5.5 (FIG. 1) and there is less overall linearity.
Figure 7:
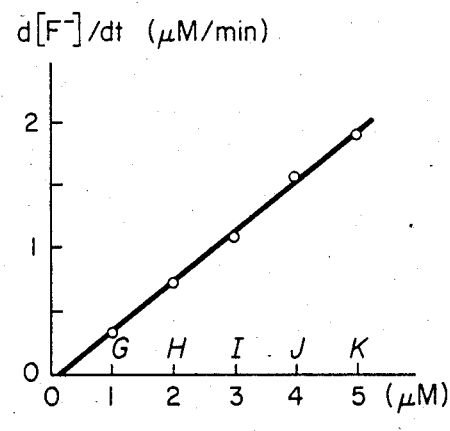
FIG. 7 is a graph in which the difference in $F^-$ concentration at 60 sec and zero second taken from the measurements summarized in FIG. 6 are plotted against actual chymotrypsin concentration of samples G to K.

In the case of chymotrypsin, the assay procedure was similar as described in Example 1, except the manner by which rate of $F^-$ generation was calculated. On the addition of DPFC solution, there was a burst of $F^-$ (FIG. 6) and it was found that linear regression could not be used for the calculation of rates. Such phenomena are well known in enzyme kinetics and are termed as "initial burst kinetics". Although sophisticated mathematical techniques can be used to evaluate rate data from such curves and would possibly be preferable such were not used in the present work for simplicity. Actually, workable conditions were established by setting up a two-point kinetic measurement, i.e. the difference in $F^-$ concentration at zero and 60 seconds. The results (pseudo slopes) corrected for the blank showed a good linear dependence in chymotrypsin concentration (see FIG. 7).

In actual analytical tests for inhibitors in serum using either trypsin or chymotrypsin at ph 7.25 as complex forming partners, the technique was identical to that disclosed in Example 1, last paragraph.

EXAMPLE 6

SERUM PROTEASE INHIBITOR CAPACITY ASSAY

Serum protease inhibitor capacity was assayed by measuring the degree of inhibition of 2.0 $\mu$M (1.46 $\mu$M active) chymotrypsin solution by serum. The difference in the relative-rates of $F^-$ generation with chymotrypsin solution and chymotrypsin solution with serum was used to estimate serum protease inhibitor capacity. The assay buffer and DPCF solution were prepared as described in Example 5. Chymotrypsin solution 2.0 $\mu$M corresponding to 1.46 $\mu$M active mass was prepared by dilution of stock chymotrypsin solution as described in Example 1.

Human serum was obtained by venipuncture from a fasting healthy volunteer. Various volumes (40–100 $\mu$l) of this serum sample were then assayed in the manner described for the chymotrypsin assay in Example 5. Reagent blanks were also measured without serum and with the corresponding volume of serum included. The serum inhibitor capacity at various serum concentrations was then calculated as $\mu$M of enzyme inhibited per liter of serum as shown in Table 3.

TABLE 3

| Chymo-trypsin | Serum Vol. $\mu$l | Rate* $F^-$ $\mu$M/min | Inhibition % | Inhibitor capacity $\mu$M/l serum |
|---|---|---|---|---|
| 2 $\mu$M | 0 | 0.73 | ≅0 | — |
| 2 $\mu$M | 40 | 0.56 | 23.3 | 42.5 |
| 2 $\mu$M | 60 | 0.50 | 31.5 | 38.3 |
| 2 $\mu$M | 80 | 0.43 | 41.5 | 37.5 |

TABLE 3-continued

| Chymo-trypsin | Serum Vol. $\mu$l | Rate* $F^-$ $\mu$M/min | Inhibition % | Inhibitor capacity $\mu$M/l serum |
|---|---|---|---|---|
| 2 $\mu$M | 100 | 0.34 | 53.4 | 38.9 |

*Corrected for blank.

Figure 8:
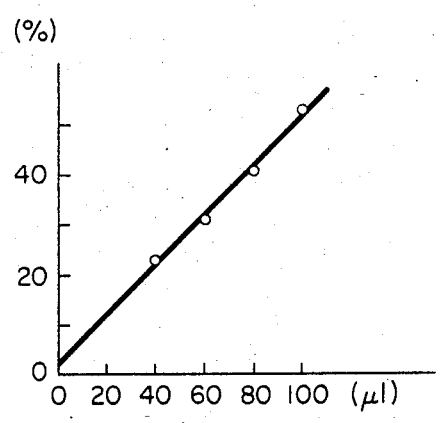
FIG. 8 is a graph similar to that of FIG. 4 but pertaining to the determination of protease inhibition in blood serum using chymotrypsin at pH 7.25.

The values measured at different serum volumes are fairly comparable, and within the range of experimental error (Mean value 39.3 $\mu$M/L Serum±2.2). Furthermore a plot of % inhibited (chymotrypsin) against volume serum in the assay showed excellent linear relationship (FIG. 8), and the intercept was nearly at zero origin.

We claim:

1. In an assay method for protease inhibitors in blood serum comprising reacting an analyte sample of said blood serum with a known excess of a 1:1 complex forming protease enzyme partner to the inhibitor of interest and thereafter back-titrating the excedent of said protease over that required to form said 1:1 complex by the reaction with diphenylcarbamyl fluoride and electrometrically determining the ionic fluoride quantitatively generated in this reaction, the improvement comprising carrying out the reaction between the protease inhibitors in the serum and the complex forming protease in the presence of a constant ionic strength buffer which maintains a constant ionic strength in the range of 0.1 to 1 and a constant pH in the range of 5 to 8 where the rate of reaction of said complex-forming protease with serum protease inhibitors or diphenylcarbamyl-fluoride is constant, and electrometrically determining the ionic fluoride generated by measuring the rate of generation of said fluoride and matching the slope of the rate curve thus obtained against standard slopes obtained identically from standard amounts of said protease.

2. The method of claim 1, characterized in that it is performed in a buffer of ionic strength 0.2 to 0.5.

3. The method of claim 2, characterized in that the pH of that buffer is 5.5 to 7.25.

4. The method of claim 1, characterized in that said complex forming protease is trypsin or $\alpha$-chymotrypsin.

5. The method of claim 2, characterized in that said buffer comprises calcium ions.

6. The method of claim 2, characterized in that said buffer comprises sodium cacodylate or sodium acetate.

7. The method of claim 2, characterized in that it is carried out in a reaction medium which contains a trace of fluoride ions to speed up electrode response.

* * * * *